(12) United States Patent
Arnin et al.

(10) Patent No.: US 10,507,045 B2
(45) Date of Patent: Dec. 17, 2019

(54) FACET DISTRACTION AND FUSION PROSTHESIS

(71) Applicant: Zygofix Ltd., Misgav (IL)

(72) Inventors: Uri Arnin, Kiryat Tivon (IL); Ofer Levy, Binyamina (IL)

(73) Assignee: Zygofix Ltd., Misgav (IL)

( * ) Notice: Subject to any disclaimer, the term of this patent is extended or adjusted under 35 U.S.C. 154(b) by 0 days.

(21) Appl. No.: 15/832,922

(22) Filed: Dec. 6, 2017

(65) Prior Publication Data

US 2019/0167316 A1  Jun. 6, 2019

(51) Int. Cl.
   *A61B 17/70* (2006.01)
   *A61B 17/00* (2006.01)
   *A61B 17/68* (2006.01)

(52) U.S. Cl.
   CPC ...... *A61B 17/7064* (2013.01); *A61B 2017/00477* (2013.01); *A61B 2017/681* (2013.01)

(58) Field of Classification Search
   CPC ............ A61B 17/7062; A61B 17/7064; A61B 2017/00477; A61B 2017/681
   USPC ................................................. 606/246–249
   See application file for complete search history.

(56) References Cited

U.S. PATENT DOCUMENTS

| 2006/0241758 | A1 | 10/2006 | Peterman |
| 2009/0326589 | A1* | 12/2009 | Lemoine ............ A61B 17/7064 606/280 |
| 2011/0060366 | A1 | 3/2011 | Heim |

FOREIGN PATENT DOCUMENTS

WO  2017/046667  3/2017

OTHER PUBLICATIONS

PCT Search and Written Opinion PCT/IB2018/059666, dated Mar. 4, 2019.

* cited by examiner

*Primary Examiner* — Julianna N Harvey
*Assistant Examiner* — Christina Negrellirodriguez
(74) *Attorney, Agent, or Firm* — Dekel Patent Ltd.; David Klein

(57) ABSTRACT

A facet distraction prosthesis includes an array of facet distraction base elements, connected to each other by a set of connector elements located at adjacent base elements. The set of connector elements includes a male connector having an at least partial cylindrical or spherical contour that is received in, and articulates with, an at least partial cylindrical or spherical recess of a female connector, so that adjacent ones of the base elements can bend in multiple degrees of freedom about different bending axes with respect to each other and adapt to a geometry of a facet joint.

9 Claims, 8 Drawing Sheets

FACET DISTRACTION AND FUSION PROSTHESIS

FIELD OF THE INVENTION

The present invention relates generally to spinal implants and prostheses, and particularly to a facet distraction and fusion prosthesis designed to be placed between the two bony elements of a spinal facet joint.

BACKGROUND OF THE INVENTION

Spinal stenosis affects a significant portion of the population. Current surgical spinal fusion uses intervertebral pedicle screws and spinal cages, designed to be connected to two or more vertebrae.

However, the use of standard cages and pedicle screws system is quite invasive, which has known negative impacts. It would be advantageous to have a system that can obtain similar pain relief and clinical outcomes in a significantly less invasive manner.

Another problem is the significant variability of the geometry of the facet joints between different patients and different spinal levels of the same patient. It is difficult to adapt the spinal implant to the varying geometry.

PCT Patent Application WO 2017/046667 describes a facet distraction prosthesis that includes an array of facet distraction base elements connected to each other by one or more connector elements. Diagonally adjacent base elements are connected to each other by a set of connector elements which intersects with another set of connector elements that connects another pair of diagonally adjacent base elements. The connector elements are flexible so that the base elements can flex with respect to each other and adapt to geometry of a facet joint.

SUMMARY OF THE INVENTION

The present invention seeks to provide an improved spinal prosthesis that can be placed between the two bony elements of a spinal facet joint and accommodate the significant variability of the geometry of the facet joints between different patients and different spinal levels of the same patient. The spinal prosthesis expands on the capabilities and structure of the prostheses of PCT Patent Application WO 2017/046667.

The clinical goal of this system is to increase the distance between the two bony elements and in this way perform indirect decompression of the spinal nerves. The system may also be firmly fixed to bones to enable long term fusion of the facet joint.

There is thus provided in accordance with an embodiment of the invention a facet distraction prosthesis including an array of facet distraction base elements, adjacent ones of the base elements being connected to each other by a set of connector elements located at the adjacent ones of the base elements, wherein the set of connector elements includes a male connector having an at least partial cylindrical or spherical contour that is received in, and articulates with, an at least partial cylindrical or spherical recess of a female connector, so that adjacent ones of the base elements can bend in multiple degrees of freedom about different bending axes with respect to each other and adapt to a geometry of a facet joint.

In accordance with another embodiment of the invention each of the base elements includes two male connectors that protrude from adjacent, perpendicular sides of the base element, and two female connectors that protrude from two other adjacent, perpendicular sides of the base element and each of the male connectors is parallel to a corresponding one of the female connectors.

In accordance with another embodiment of the invention for each the set of connector elements, the male connector and the female connector form a ball and socket joint.

In accordance with another embodiment of the invention for each the set of connector elements, the male connector and the female connector form a universal joint.

In accordance with another embodiment of the invention for each the set of connector elements, the male connector and the female connector form a pin joint.

In accordance with another embodiment of the invention for each of the base elements, the male connector is part of the base element.

In accordance with another embodiment of the invention for each of the base elements, the male connector is not part of the base element.

In accordance with another embodiment of the invention for each the set of connector elements, the male connector is a cross of two cylindrical elements.

In accordance with another embodiment of the invention for each the set of connector elements, there are at least two female connectors that are axially separated from each other.

One or more keels may extend from upper and/or lower faces of the base elements.

BRIEF DESCRIPTION OF THE DRAWINGS

The present invention will be understood and appreciated more fully from the following detailed description, taken in conjunction with the drawings in which.

DETAILED DESCRIPTION

Figure 1A:
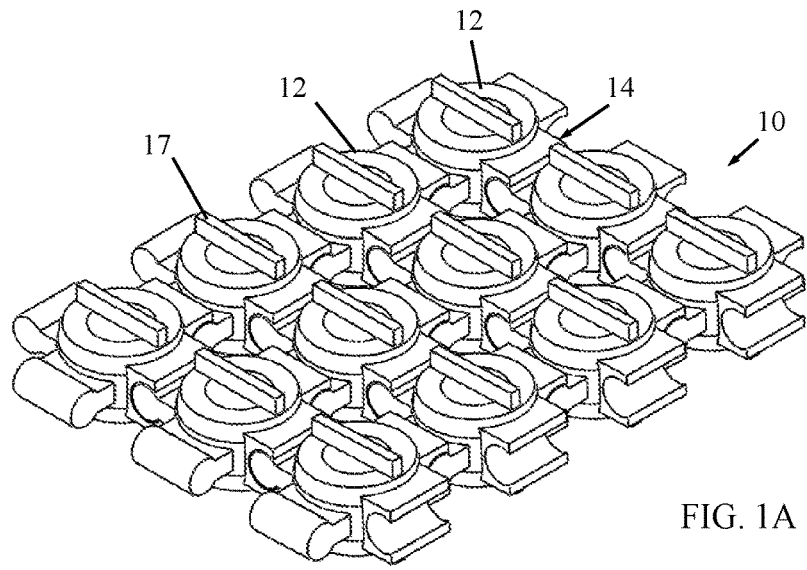
FIG. 1A is a simplified pictorial illustration of a facet distraction prosthesis, constructed and operative in accordance with a non-limiting embodiment of the present invention, with cylindrical connector elements.

Reference is now made to FIGS. 1A-1F, which illustrate a facet distraction and fusion prosthesis 10, constructed and operative in accordance with a non-limiting embodiment of the present invention.

The facet distraction prosthesis 10 includes an array of facet distraction base elements 12, adjacent base elements 12 being connected to each other by a set of connector elements 14, which are located at adjacent base elements.

The set of connector elements 14 includes a male connector 16 having an at least partial cylindrical contour 18 that is received in, and articulates with, an at least partial cylindrical recess 22 of a female connector 24. In this manner, adjacent base elements 12 can flex with respect to each other and adapt to geometry of a facet joint.

Base elements of all embodiments may have any geometrical shape, such as but not limited to, circular, elliptic, round, square, rectangular, triangular, hexagonal, polygonal irregular, etc.

Connector elements of all embodiments may be made of the same material as base elements 12 or of a different material. The materials include, without limitation, a stainless steel alloy, titanium alloy, shape memory or superelastic material, plastic and others, or any combination thereof.

Figure 1B:
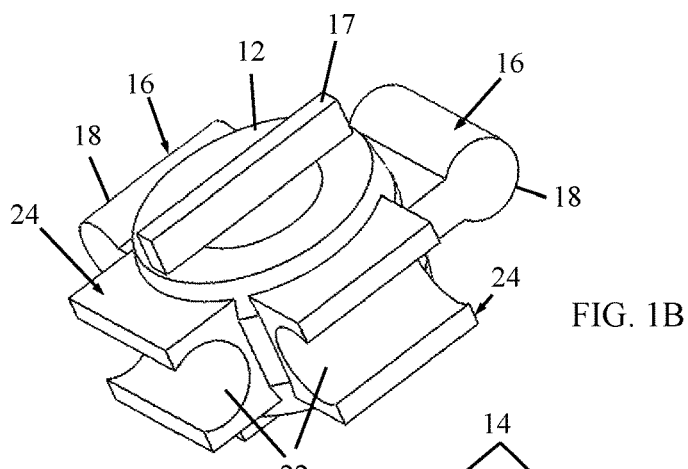
FIG. 1B is a simplified pictorial illustration of a base element of the facet distraction prosthesis of FIG. 1A.
Figure 1C:
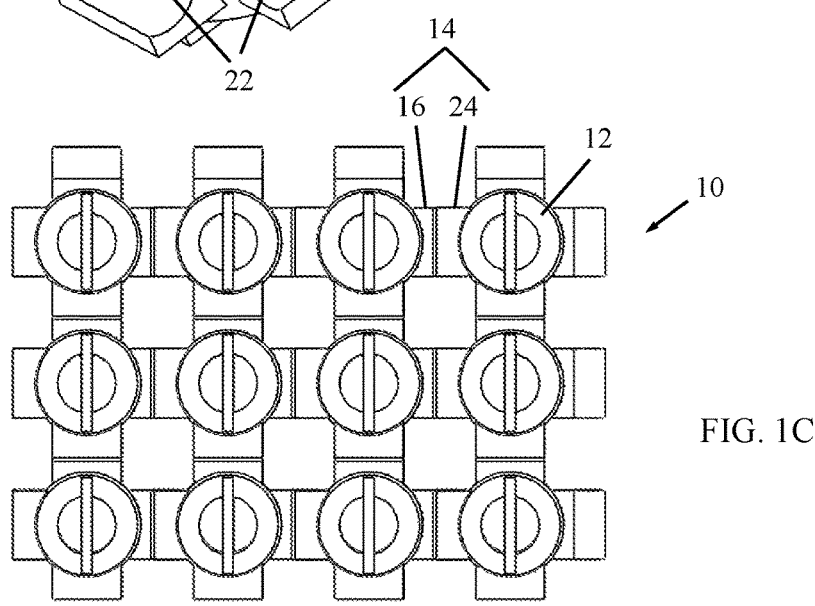
FIG. 1C is a simplified plan view illustration of the facet distraction prosthesis of FIG. 1A.
Figure 1D:
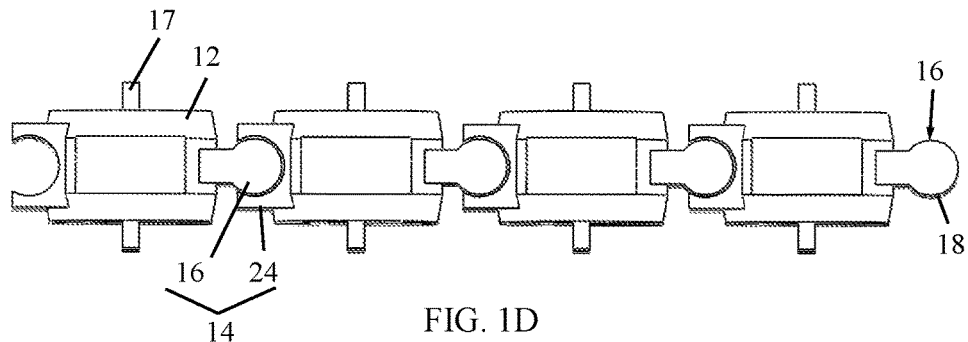
FIG. 1D is a simplified side view illustration of the facet distraction prosthesis of FIG. 1A.
Figure 1E:
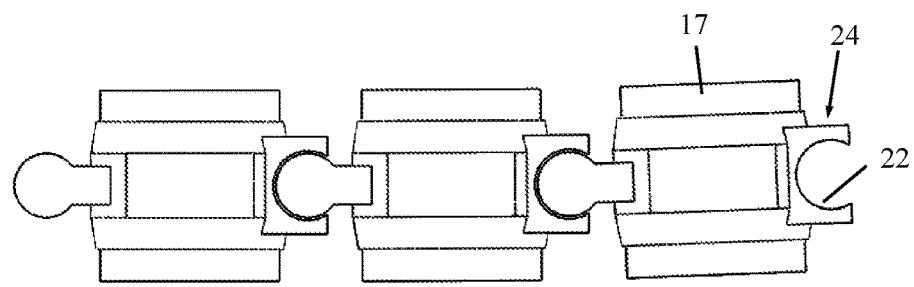
FIG. 1E is a simplified front view illustration of the facet distraction prosthesis of FIG. 1A.

As seen best in FIG. 1B, each base element 12 may have two male connectors 16 that protrude from adjacent, perpendicular sides of base element 12, and two female connectors 24 that protrude from two other adjacent, perpendicular sides of base element 12. One male connector 16 is parallel to one female connector 24.

Figure 1F:
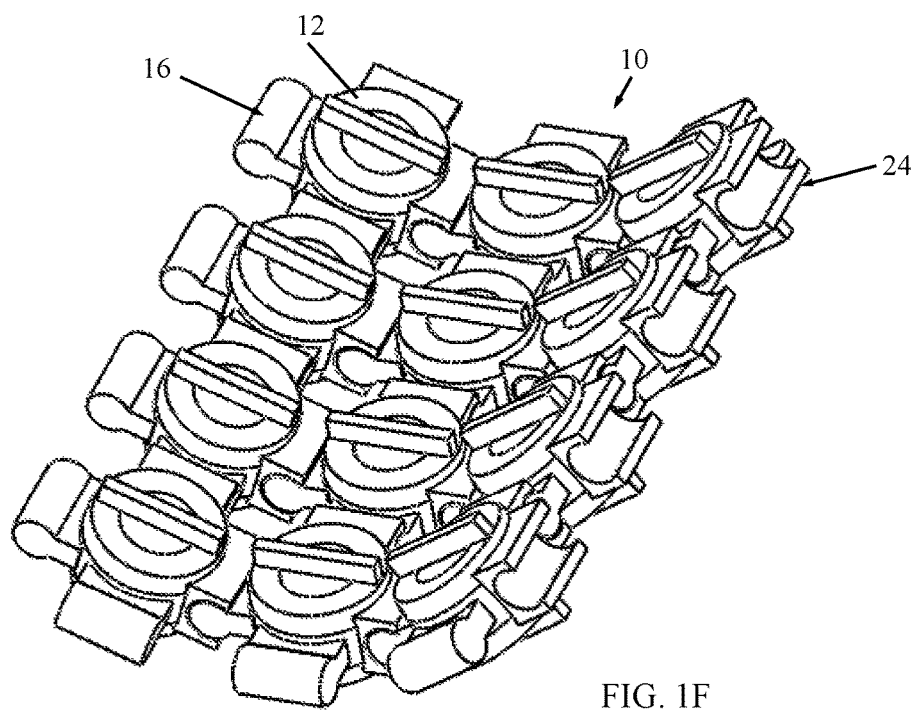
FIG. 1F is a simplified pictorial illustration of the facet distraction prosthesis of FIG. 1A in a bent orientation.
Figure 2A:
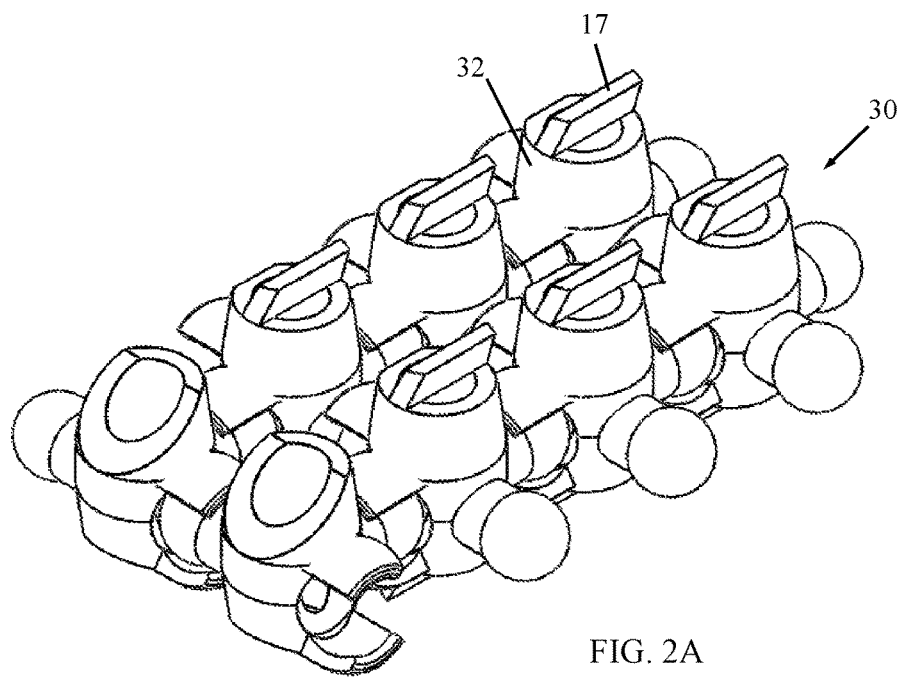
FIG. 2A is a simplified pictorial illustration of a facet distraction prosthesis, constructed and operative in accordance with another non-limiting embodiment of the present invention, with spherical connector elements (e.g., ball and socket joints)
Figure 2B:
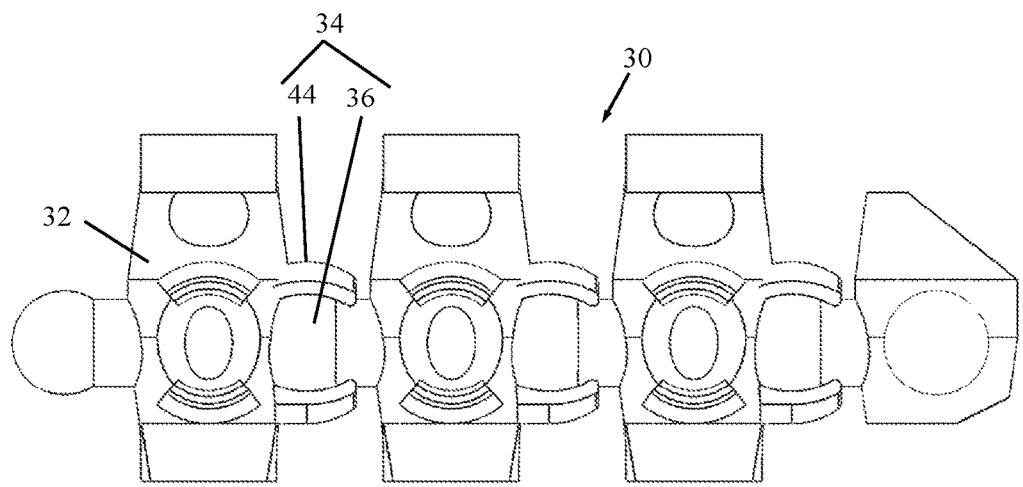
FIG. 2B is a simplified side view illustration of the facet distraction prosthesis of FIG. 2A.
Figure 2C:
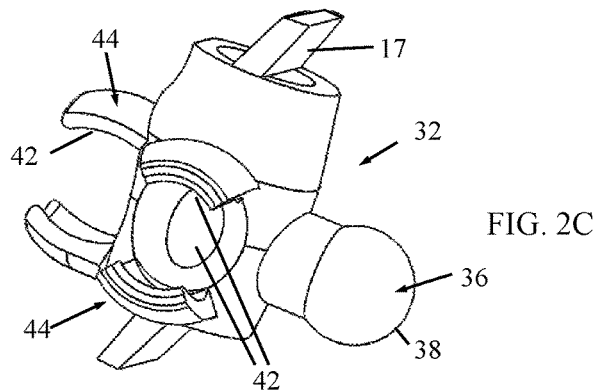
FIG. 2C is a simplified pictorial illustration of a base element of the facet distraction prosthesis of FIG. 2A.
Figure 2D:
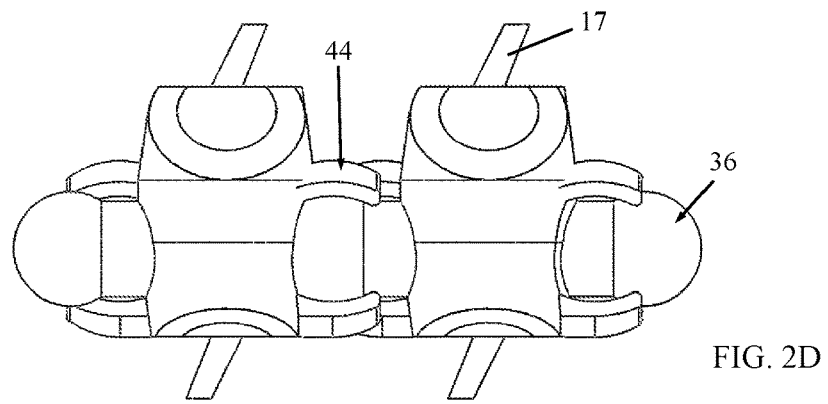
FIG. 2D is a simplified front view illustration of the facet distraction prosthesis of FIG. 2A.
Figure 2E:
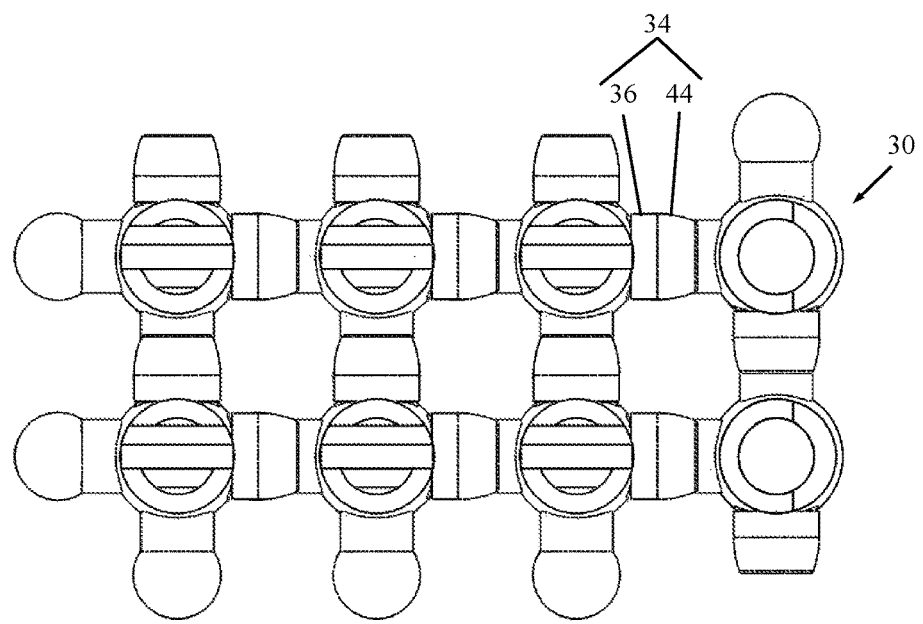
FIG. 2E is a simplified plan view illustration of the facet distraction prosthesis of FIG. 2A.
Figure 3A:
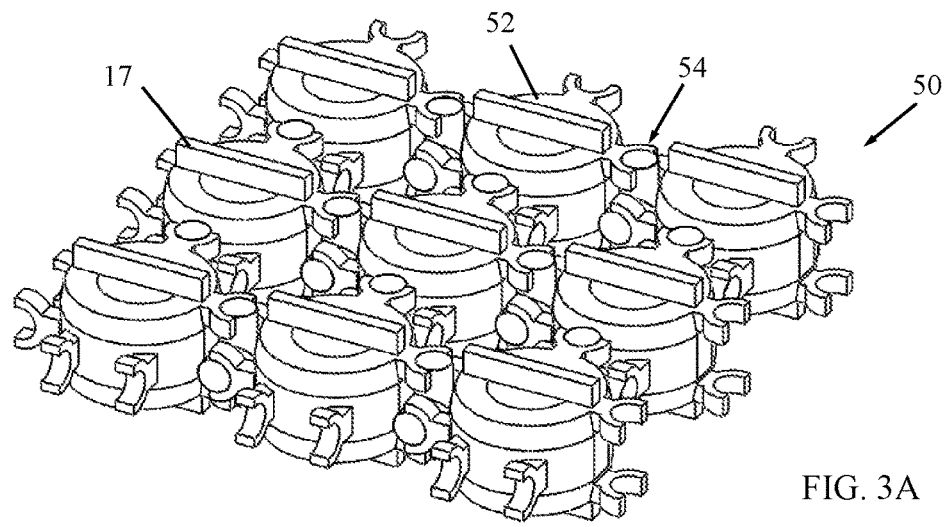
FIG. 3A is a simplified pictorial illustration of a facet distraction prosthesis, constructed and operative in accordance with another non-limiting embodiment of the present invention, with universal joint connector elements.
Figure 3B:
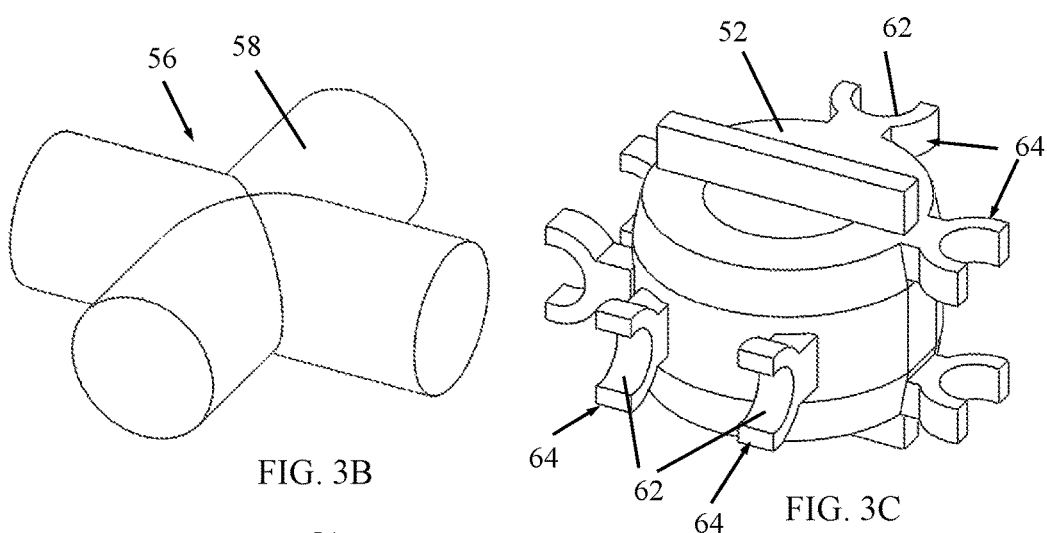
FIG. 3B is a simplified pictorial illustration of a male connector element of the facet distraction prosthesis of FIG. 3A.
Figure 3C:
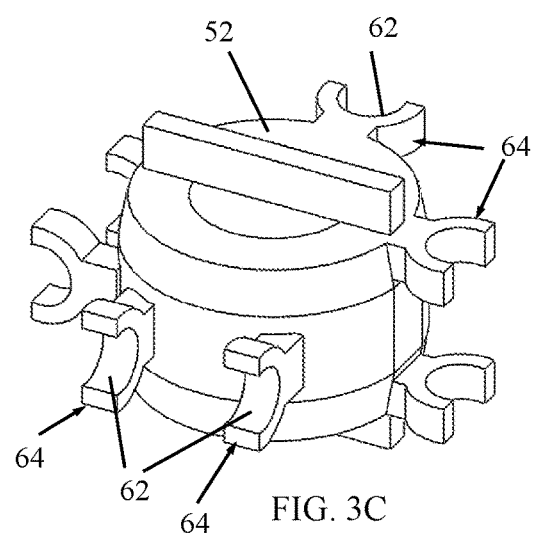
FIG. 3C is a simplified pictorial illustration of a base element of the facet distraction prosthesis of FIG. 3A.
Figure 3D:
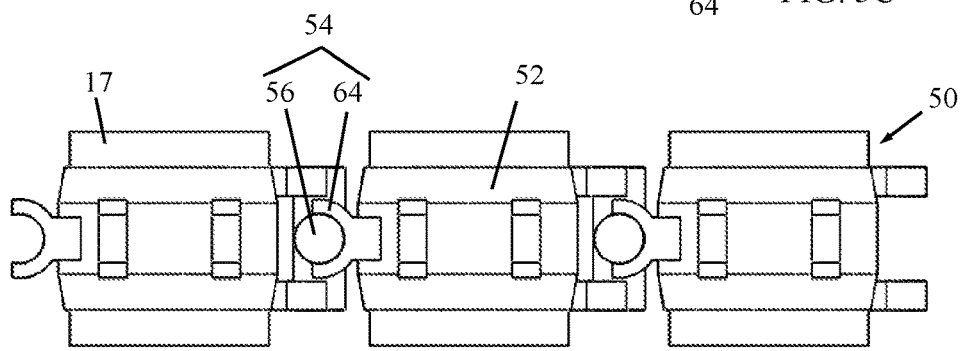
FIG. 3D is a simplified side view illustration of the facet distraction prosthesis of FIG. 3A.
Figure 3E:
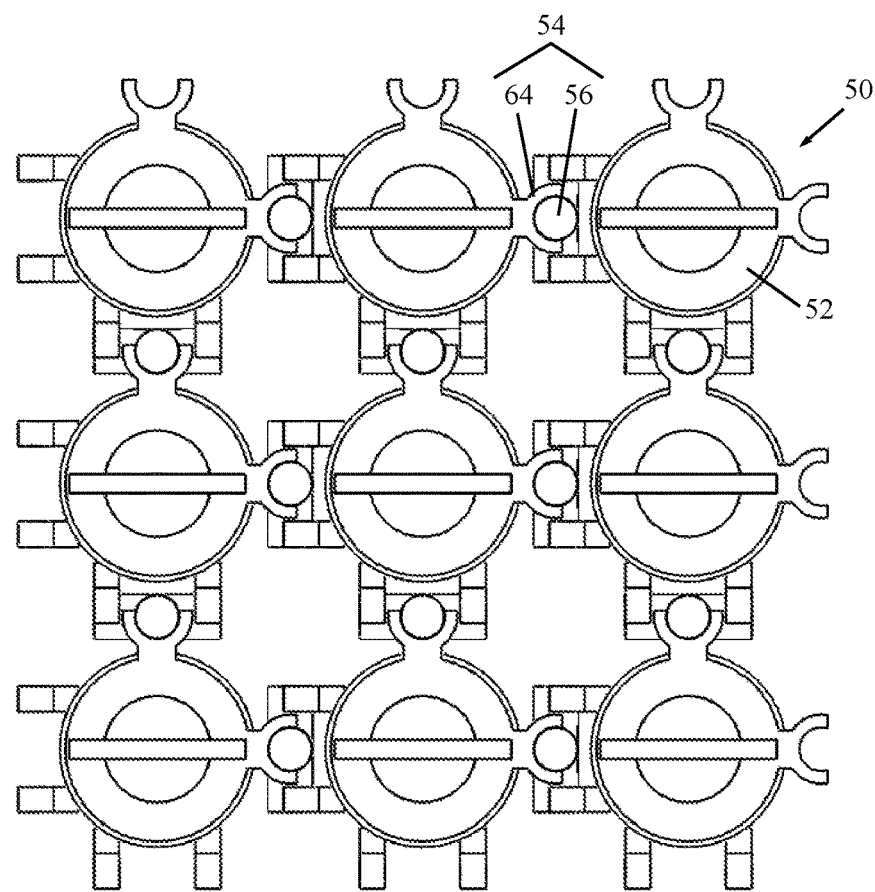
FIG. 3E is a simplified plan view illustration of the facet distraction prosthesis of FIG. 3A.
Figure 3F:
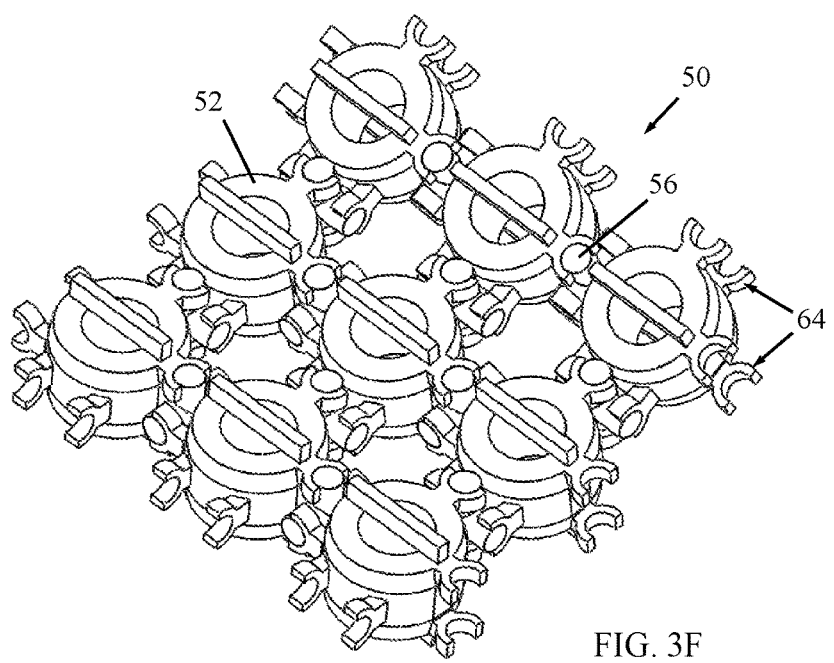
FIG. 3F is a simplified pictorial illustration of the facet distraction prosthesis of FIG. 3A in a bent orientation.
Figure 4A:
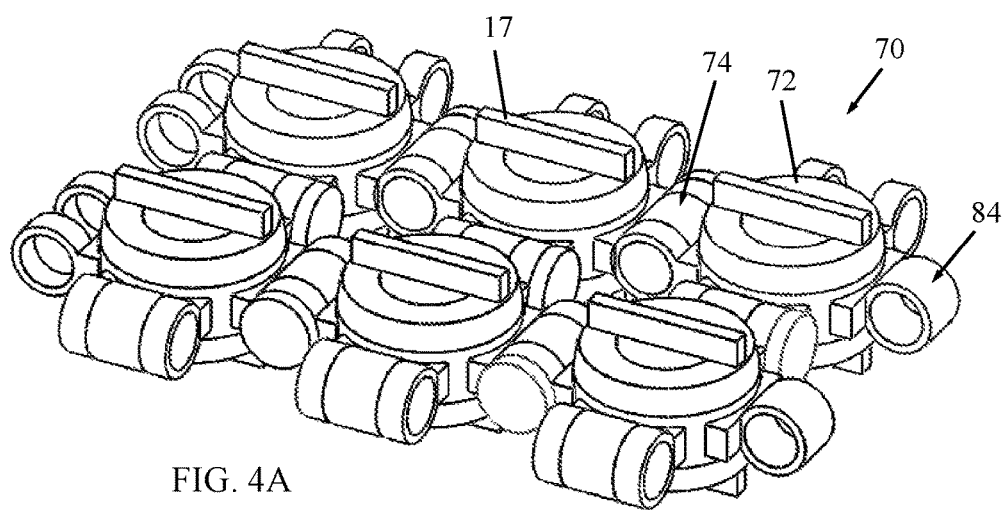
FIG. 4A is a simplified pictorial illustration of a facet distraction prosthesis, constructed and operative in accordance with another non-limiting embodiment of the present invention, with pin joint connector elements.
Figure 4B:
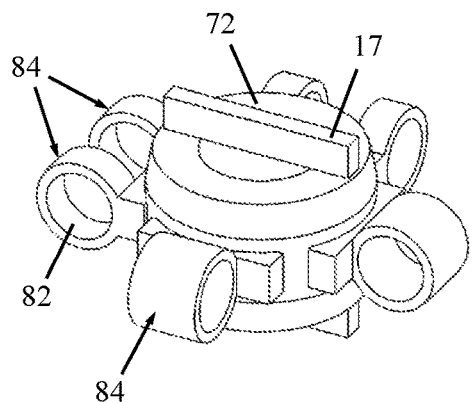
FIG. 4B is a simplified pictorial illustration of a base element of the facet distraction prosthesis of FIG. 4A.
Figure 4C:
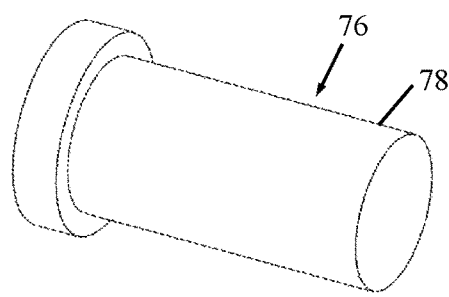
FIG. 4C is a simplified pictorial illustration of a male connector element of the facet distraction prosthesis of FIG. 4A.
Figure 4D:
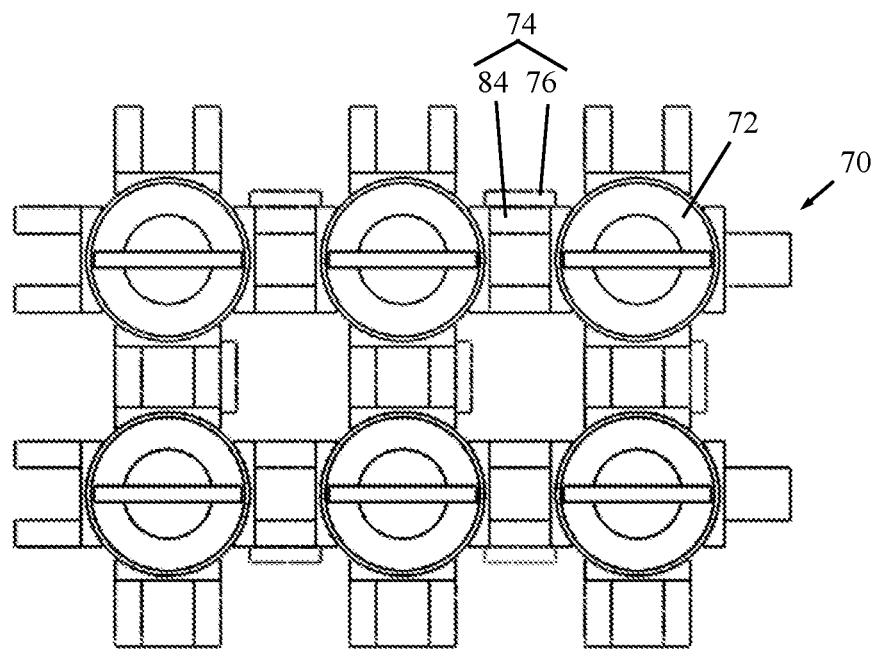
FIG. 4D is a simplified plan view illustration of the facet distraction prosthesis of FIG. 4A.
Figure 4E:
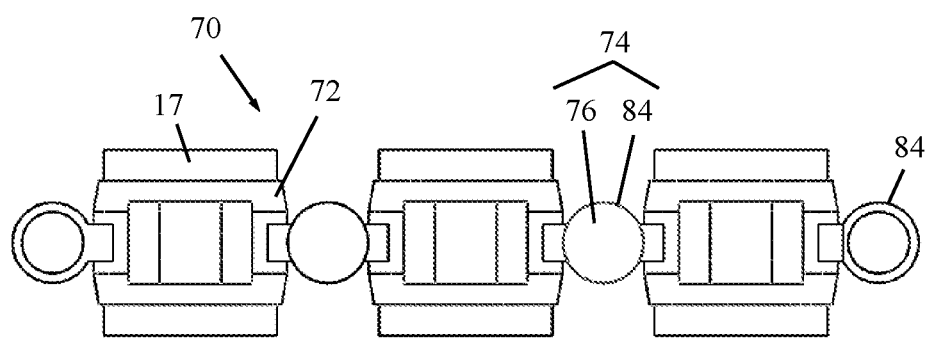
FIG. 4E is a simplified side view illustration of the facet distraction prosthesis of FIG. 4A.

FIGS. 1A and 1F illustrate facet distraction prosthesis 10 in flat and bent orientations, respectively. In the bent orientation, the prosthesis can bend in multiple degrees of freedom about different bending axes.

The facet distraction prosthesis 10, as well as the other embodiments of the invention, may include one or more keels 17 extending from upper and/or lower faces of the base elements, which bite into spinal structure for increasing the holding force that holds the prosthesis in place in the spinal structure. As seen in FIGS. 1A-1F and other embodiments, keels 17 may be perpendicular to the top or bottom surfaces of the base element 12. In the embodiment of FIGS. 2A-2E, keels 17 may be tilted and non-perpendicular to the top or bottom surfaces of the base element 12. The keels may be shaped to be easily inserted but difficult to be pulled back, in order to prevent migration.

Reference is now made to FIGS. 2A-2E, which illustrate a facet distraction and fusion prosthesis 30, constructed and operative in accordance with a non-limiting embodiment of the present invention.

The facet distraction prosthesis 30 includes an array of facet distraction base elements 32, adjacent base elements 32 being connected to each other by a set of connector elements 34, which are located at adjacent base elements.

The set of connector elements 34 includes a male connector 36 having an at least partial spherical contour 38 that is received in, and articulates with, an at least partial spherical recess 42 of a female connector 44, thereby forming a ball and socket joint. In this manner, adjacent base elements 32 can flex with respect to each other and adapt to geometry of a facet joint.

Each base element 32 may have two male connectors 36 that protrude from adjacent, perpendicular sides of base element 32, and two female connectors 44 that protrude from two other adjacent, perpendicular sides of base element 32. One male connector 36 is parallel to one female connector 44.

Reference is now made to FIGS. 3A-3F, which illustrate a facet distraction and fusion prosthesis 50, constructed and operative in accordance with a non-limiting embodiment of the present invention.

The facet distraction prosthesis 50 includes an array of facet distraction base elements 52, adjacent base elements 52 being connected to each other by a set of connector elements 54, which are located at adjacent base elements.

The set of connector elements 54 includes a male connector 56 having a cylindrical contour 58 that is received in, and articulates with, an at least partial cylindrical recess 62 of a female connector 64. The male connector 56 is a cross of two cylindrical elements, which by articulating with the recesses 62 of female connector 64, forms a universal joint. In this manner, adjacent base elements 52 can flex with respect to each other and adapt to geometry of a facet joint.

Unlike the previous two embodiments, in this embodiment the male connector 56 is not part of the base element, but is located at the base element.

Each base element 52 may have two female connectors 64 that are separated from each other along a vertical axis and another two female connectors 64 that are separated from each other along a vertical axis on adjacent, perpendicular sides of base element 52. Each base element 52 may have two female connectors 64 that are separated from each other along a horizontal axis and another two female connectors 64 that are separated from each other along a horizontal axis on adjacent, perpendicular sides of base element 52.

Reference is now made to FIGS. 4A-4E, which illustrate a facet distraction and fusion prosthesis 70, constructed and operative in accordance with a non-limiting embodiment of the present invention.

The facet distraction prosthesis 70 includes an array of facet distraction base elements 72, adjacent base elements 72 being connected to each other by a set of connector elements 74, which are located at adjacent base elements.

The set of connector elements 74 includes a male connector 76 having a cylindrical contour 78 that is received in, and articulates with, a cylindrical recess 82 of a female connector 84. The male connector 76 is a pin that forms a pivot joint when inserted in the recesses 82 of female connector 84. In this manner, adjacent base elements 72 can flex with respect to each other and adapt to geometry of a facet joint.

As in the embodiment of FIGS. 3A-3F, in this embodiment the male connector 76 is not part of the base element, but is located at the base element.

Each base element 72 may have two female connectors 84 that are axially separated from each other and another two female connectors 84 that are axially separated from each other on adjacent, perpendicular sides of base element 72. Each base element 72 may have one relatively longer female connector 84 and another relatively longer female connector 84 on adjacent, perpendicular sides of base element 72. The relatively longer female connectors 84 fit into the gap between the female connectors 84 that are axially separated from each other.

The facet distraction prostheses of the invention may have a leading face that first enters the area of the facet joints when installing the prosthesis. The leading face may have a tapered shape as in FIG. 2B, which facilitates insertion of the prosthesis. The joint member at the trailing face may be used for grasping the prosthesis for easy retrieval, adjustment or withdrawal.

It is noted that any of the embodiments of the invention may be filled with bone graft to promote fusion of the bony elements to each other.

The invention claimed is:

1. A joint prosthesis comprising:
   an array of facet distraction base elements, adjacent ones of said base elements being connected to each other by a set of connector elements located at said adjacent ones of said base elements;
   wherein said set of connector elements comprises a male connector having an at least partial cylindrical or spherical contour that is received in, and articulates with, an at least partial cylindrical or spherical recess of a female connector, so that adjacent ones of said base elements can bend in multiple degrees of freedom about different bending axes with respect to each other and adapt to a geometry of a facet joint, wherein each of said base elements comprises two male connectors that protrude from adjacent, perpendicular sides of said base element, and two female connectors that protrude from two other adjacent, perpendicular sides of said base element and each of said male connectors is parallel to a corresponding one of said female connectors.

2. The joint prosthesis according to claim 1, wherein for each said set of connector elements, said male connector and said female connector form a ball and socket joint.

3. The joint prosthesis according to claim 1, wherein for each said set of connector elements, said male connector and said female connector form a universal joint.

4. The joint prosthesis according to claim 1, wherein for each said set of connector elements, said male connector and said female connector form a pin joint.

5. The joint prosthesis according to claim 1, wherein for each of said base elements, said male connector is part of said base element.

6. The joint prosthesis according to claim 1, wherein for each of said base elements, said male connector is not part of said base element.

7. The joint prosthesis according to claim 1, wherein for each said set of connector elements, said male connector is a cross of two cylindrical elements.

8. The joint prosthesis according to claim 1, wherein for each said set of connector elements, there are at least two female connectors that are axially separated from each other.

9. The joint prosthesis according to claim 1, further comprising one or more keels that extend from upper or lower faces of said base elements.

* * * * *